(12) United States Patent
Hamamoto et al.

(10) Patent No.: US 6,890,739 B1
(45) Date of Patent: May 10, 2005

(54) USE OF URIDINE DIPHOSPHATE GLUCOSE 4-EPIMERASE

(75) Inventors: Tomoki Hamamoto, Choshi (JP); Toshitada Noguchi, Choshi (JP)

(73) Assignee: Yamasa Corporation, Chiba (JP)

( * ) Notice: Subject to any disclaimer, the term of this patent is extended or adjusted under 35 U.S.C. 154(b) by 288 days.

(21) Appl. No.: 10/130,785

(22) PCT Filed: Nov. 22, 2000

(86) PCT No.: PCT/JP00/08245

§ 371 (c)(1),
(2), (4) Date: May 23, 2002

(87) PCT Pub. No.: WO01/38555

PCT Pub. Date: May 31, 2001

(30) Foreign Application Priority Data

Nov. 25, 1999 (JP) ............................................ 11-333610

(51) Int. Cl.$^7$ ............................ C12P 19/38; C12N 9/90
(52) U.S. Cl. ......................................... 435/87; 435/233
(58) Field of Search ................................... 435/87, 233

(56) References Cited

U.S. PATENT DOCUMENTS 4,569,909 A    2/1986   Seno et al. .................... 435/89

FOREIGN PATENT DOCUMENTS

EP           0 096 547        12/1983

OTHER PUBLICATIONS

Kunst, F., et al. (1997) Nature 390, 249–256.*
Schroegel, O., et al. (1996) Acc, No. P55180.*
Ken–ichi Yoshida et al., "Sequencing of a 65 kb region of the *Bacillus subtilis* genome containing the *lic* and *cel loci*, and creation of a 177 kb contig covering the *gnt–sac*XY region", Microbiology, vol. 142, pp. 3113–3123, 1996.
Kenji Yamamoto et al., "Purification and some Properties of UDP–N–Acetyglucosamine 4–Epimerase from *Bacillus subtilis*", Agric. Biol. Chem., vol. 49, No. 3, pp. 603–609, 1985.

Friedrich Piller et al., "Co–purifiacation and Characterization of UDP–glucose 4–Epimerase and UDP–N–acetylglucosamine 4–Epimerase from Porcine Submaxillary Glands", The Journal of Biological Chemistry, vol. 258, No. 17, pp. 10774–10778, Sep. 10, 1983.
Luis Glaser, "The Biosynthesis of N–Acetylgalactosamine", The Journal of Biological Chemistry, vol. 234, No. 11, pp. 2801–2805, Nov. 1959.
Robert A. Darrow et al., "Purification and Properties of Uridine Diphosphate Galactose 4–Epimerase from Yeast", Biochemistry, vol. 7, No. 5, pp. 1645–1654, May 1968.
David B. Wilson et al., "The Enzymes of the Galactose Operon in *Escherichia coli*", The Journal of Biological Chemistry, vol. 244, No. 8, pp. 2132–2136, Apr. 25, 1969.
Friedrich Piller et al., "The Preparation of UPD–N–Acetylgalactosamine from UDP–N–Acetylglucosamine Employing UDP–N–Acetylglucosamine–4–Epimerase$^1$", Analytical Biochemistry, vol. 127, pp. 171–177, 1982.
B. B. Quimby et al., "Characterization of two Mutations Associated with Epimerase–Deficiency Galactosemia, by use of a Yeast Expression System for Human UDP–Galactose–4–Epimerase", Am. J. Hum. Genet., vol. 61, pp. 590–598, 1997.
Databse Swissport, Oct. 1, 1996, Schrogel et al. UDP–glucose 4–epimerase, Database Accession No. P55180, XP002235638 *abstract*.

* cited by examiner

*Primary Examiner*—Charles L. Patterson, Jr.
(74) *Attorney, Agent, or Firm*—Wenderoth, Lind & Ponack, L.L.P.

(57) ABSTRACT

The present invention relates to a new use of uridine diphosphate glucose 4-epimerase (also called uridine diphosphate galactose 4-epimerase), and a method of converting uridine diphosphate N-acetylglucosamine (UDP-GlcNAc) to uridine diphosphate N-acetylgalactosamine (UDP-GalNAc) by using the said enzyme. The process for producing UDP-GalNAc by using the uridine diphosphate glucose 4-epimerase and the UDP-GalNAc supply system according to the present invention are practical and efficient, and greatly beneficial to the industries.

18 Claims, No Drawings

SEQUENCE LISTING

<160> NUMBER OF SEQ ID NOS: 3

<210> SEQ ID NO 1
<211> LENGTH: 339
<212> TYPE: PRT
<213> ORGANISM: Bacillus subtilis

<400> SEQUENCE: 1

```
Met Ala Ile Leu Val Thr Gly Gly Ala Gly Tyr Ile Gly Ser His Thr
                 5                  10                  15

Cys Val Glu Leu Leu Asn Ser Gly Tyr Glu Ile Val Leu Asp Asn
             20                  25                  30

Leu Ser Asn Ser Ser Ala Glu Ala Leu Asn Arg Val Lys Glu Ile Thr
             35                  40                  45

Gly Lys Asp Leu Thr Phe Tyr Glu Ala Asp Leu Leu Asp Arg Glu Ala
         50                  55                  60

Val Asp Ser Val Phe Ala Glu Asn Glu Ile Glu Ala Val Ile His Phe
 65                  70                  75                  80

Ala Gly Leu Lys Ala Val Gly Glu Ser Val Ala Ile Pro Leu Lys Tyr
                 85                  90                  95

Tyr His Asn Asn Leu Thr Gly Thr Phe Ile Leu Cys Glu Ala Met Glu
            100                 105                 110

Lys Tyr Gly Val Lys Lys Ile Val Phe Ser Ser Ala Thr Val Tyr
            115                 120                 125

Gly Val Pro Glu Thr Ser Pro Ile Thr Glu Asp Phe Pro Leu Gly Ala
        130                 135                 140

Thr Asn Pro Tyr Gly Gln Thr Lys Leu Met Leu Glu Gln Ile Leu Arg
145                 150                 155                 160

Asp Leu His Thr Ala Asp Asn Glu Trp Ser Val Ala Leu Leu Arg Tyr
                165                 170                 175

Phe Asn Pro Phe Gly Ala His Pro Ser Gly Arg Ile Gly Glu Asp Pro
            180                 185                 190

Asn Gly Ile Pro Asn Asn Leu Met Pro Tyr Val Ala Gln Val Ala Val
            195                 200                 205

Gly Lys Leu Glu Gln Leu Ser Val Phe Gly Asn Asp Tyr Pro Thr Lys
        210                 215                 220

Asp Gly Thr Gly Val Arg Asp Tyr Ile His Val Val Asp Leu Ala Glu
225                 230                 235                 240

Gly His Val Lys Ala Leu Glu Lys Val Leu Asn Ser Thr Gly Ala Asp
                245                 250                 255

Ala Tyr Asn Leu Gly Thr Gly Thr Gly Tyr Ser Val Leu Glu Met Val
            260                 265                 270

Lys Ala Phe Glu Lys Val Ser Gly Lys Glu Val Pro Tyr Arg Phe Ala
        275                 280                 285

Asp Arg Arg Pro Gly Asp Ile Ala Thr Cys Phe Ala Asp Pro Ala Lys
    290                 295                 300

Ala Lys Arg Glu Leu Gly Trp Glu Ala Lys Arg Gly Leu Glu Glu Met
305                 310                 315                 320

Cys Ala Asp Ser Trp Arg Trp Gln Ser Ser Asn Val Asn Gly Tyr Lys
                325                 330                 335

Ser Ala Glu
        339
```

```
<210> SEQ ID NO 2
<211> LENGTH: 28
<212> TYPE: DNA
<213> ORGANISM: Artificial Sequence
<220> FEATURE:
<223> OTHER INFORMATION: Primer for amplification of galE gene

<400> SEQUENCE: 2
gatctagaaa cctctatcga attgctgg                                        28

<210> SEQ ID NO 3
<211> LENGTH: 30
<212> TYPE: DNA
<213> ORGANISM: Artificial Sequence
<220> FEATURE:
<223> OTHER INFORMATION: Primer for amplification of galE gene

<400> SEQUENCE: 3
aactgcaggc ctccattctt attccgcact                                      30
```

USE OF URIDINE DIPHOSPHATE GLUCOSE 4-EPIMERASE

TECHNICAL FIELD

The present invention relates to a new use of uridine diphosphate glucose 4-epimerase (also called uridine diphosphate galactose 4-epimerase), and a method of converting uridine diphosphate N-acetylglucosamine (UDP-GlcNAc) to uridine diphosphate N-acetylgalactosamine (UDP-GalNAc) by making use of the above enzyme.

BACKGROUND ART

Recent remarkable progress of molecular and biochemical researches on sugar chains has clarified some of sugar's important molecular and function and role, which makes it possible to develop pharmaceuticals sugar chains, and functional materials based on the sugar chains (oligosaccharides) possessing physiological activities. However, the oligosaccharides which are commercially available as reagents at present are limited to a few types and, to boot, very expensive. Moreover, such oligosaccharides are produced only on a reagent level and can not be supplied in large quantities.

Conventionally, oligosaccharides have been produced by such methods as extraction from natural substances, chemical synthesis, enzymatic synthesis, and combinations of these methods, but enzymatic synthesis has been considered best suited for their large-scale production as medicinal or functional materials.

This is because the enzymatic synthesis method is considered advantageous over the other methods in that (1) this method dose not require intricate steps for protection and deprotection such as necessary in the chemical synthesis method, and is also capable of quickly synthesizing the objective oligosaccharide, and (2) it is possible with this method to synthesize oligosaccharides having highly structural specificity because of substrate specificity of the enzyme used. Further, recent progress of biotechnology such as recombinant DNA technology have made it possible to mass-produce various types of enzyme economically, also contributing to establishing the superiority of enzymatic synthesis.

Two methods for the synthesis of oligosaccharides by enzymatic synthesis are available: (1) a reverse reaction of the hydrolase of an oligosaccharide is utilized, and (2) a glycosyltransferase is utilized. The former method has the advantage in that inexpensive monosaccharide can be used as substrate, but because it employs the reverse reaction to the hydrolysis, its practical application is very difficult in respects of yield of synthesis and applicability to the syntheses of oligosaccharides having a complicated structure.

On the other hand, the latter method, which utilizes a specific glycosyltransferase, is considered advantageous over the former method in that this method can be applied to the production of oligosaccharides having a complicated structure and is also high in yield of synthesis. Moreover, mass-production of various glycosyltransferases made possible by the recent progress of biotechnology such as recombinant DNA technology is contributing to the realization of practical application of said method.

However, sugar nucleotides, which are generally used as a sugar donor, are still expensive except for a few types thereof and actually supplied only in small amounts on reagent levels. For instance, regarding UDP-GalNAc which is a donor of N-acetylgalactosamine contained in the core portion of sugar chain of O-bound glycoprotein or sphingoglycolipid, there has been reported a method for synthesizing this compound from UDP-GlcNAc by using uridine diphosphate N-acetylglycosamine 4-epimerase (UDP-GlcNAc 4-epimerase) derived from animal tissue or *Bacillus subtilis*. (Analytical Biochemistry, 127, 171–177 (1982); J. Biol. Chem., 234(11), 2801–2805 (1959); JP-A-7-79792).

However, although UDP-GlcNAc is a sugar nucleotide which is relatively easy to prepare in large quantities. UDP-GlcNAc 4-epimerase exists only in small quantities in the animal tissues or bacterial cells. Also, there has been no report of preparation of this enzyme by recombinant DNA technology using an UDP-GlcNAc 4-epimerase gene. Thus, it has been practically difficult to produce UDP-GalNAc by making use of said enzyme, let alone bulk preparation of this enzyme itself.

DISCLOSURE OF THE INVENTION

As a result of intensive studies for eliminating the above problems, the present inventors found that quite surprisingly uridine diphosphate glucose 4-epimerase (UDP-glucose 4-epimerase) derived from a *Bacillus subtilis* not only has an activity to catalyze the essential interconversion reaction of formula (1) but also has an activity to catalyze the interconversion reaction of formula (2).

(1) UPD-glucose ↔ DUP-galactose
(2) UDP-GlcNfAc ↔ UDP-GalNAc

It has already been reported that mammalian UDP-glucose 4-eipemerase has both an activity to catalyze the interconversion reaction of formula (1) and an activity to catalyze the interconversion reaction of formula (2). (The Journal of Biological Chemistry, Vol. 258, No. 17, 10774–10778 (1983); Am. J. Hum. Genet, 61, 590–598 (1997)).

The method using the said enzyme, however, is impractical for the reasons, for example, that the production of UDP-glucose 4-epimerase derived from animal tissues is scant, and it is difficult to prepare this enzyme, and that expensive nicotinamide adenine dinucleotide (NAD*) needs to be used as coenzyme in carrying out the interconversion reaction using said enzyme.

On the other hand, it has been reported that UDP-glucose 4-epimerase derived from *Escherichia coli* and yeast has no activity to catalyze the conversion reaction from UDP-GlcNAc to UDP-GalNAc (J. Biol. Chem., 244, 2132–2136 (1969); Biochemistry, 7, 1645–1654 (1968); The Journal of Biological Chemistry, Vol. 258, No. 17, 10774–10778 (1983); Am. J. Hum. Genet., 61, 590–598 (1997)), and that UDP-glucose 4-epimerase derived from *Bacillus subtilis* and UDP-GlcNAc 4-pimerase from *Bacillus subtilis* are the completely different enzymes (J. Biol. Chem., 234 (11), 2801–2805 (1959): Chemistry, Vol. 258, No. 17, 10774–10778 (1983)), so that it has been quite unexpected to reach the finding that UDP-glucose 4-epimerase derived from *Bacillus subtilis* has an activity to catalyze not only the conversion reaction of from UDP-glucose to UDP-galactose but also the conversion reaction of from UDP-GlcNAc to UDP-GalNAc.

Our further researches founded on the above finding have led to the disclosure of the fact that UDP-glucose 4-epimerase derived from not only *Bacillus subtilis* but also other bacteria having a spore forming faculty has an activity to catalyze the conversion reactions of from UDP-glucose to UDP-galactose and from UDP-GlcNAc to UDP-GalNAc.

The present invention has been attained on the basis of this novel disclosure.

The present invention relates to a method of converting UDP-GlcNAc to UDP-GalNAc by using an epimerase, said epimerase being UDP-glucose 4-epimerase derived from a spore forming becterium.

The present invention also relates to an UDP-GalNAc supply system comprising UDP-GlcNAc and UDP-glucose 4-epimerase derived from a spore-forming bacterium.

Further, the present invention relates to a process for producing UDP-GalNAc by acting an epimerase to UDP-GlcNAc, said epimerase being UDP-glucose 4-empimerase derived from a spore-forming bacterium.

Still further, the present invention relates to a method of converting UDP-GlcNAc to UDP-GalNAc by using an epimerase, said epimerase being one having an amino acid sequence indicated by SEQ ID NO: 1 in the Sequence Listing, or one having an amino acid sequence of SEQ ID NO: 1 which has undergone deletion, substitution and/or addition of one to several amino acid residues, and also having the same enzyme activity as the epimerase having the amino acid sequence of SEQ ID NO: 1.

The present invention also relates to an UDP-GalNAc supply system comprising UDP-GlcNAc and an epimerase having an amino acid sequence indicated by SEQ ID NO: 1 in the Sequence Listing, or an epimerase having an amino acid sequence of SEQ ID NO: 1 which has undergone deletion, substitution and/or addition of one to several amino acid residues, and also having the same enzyme activity as the epimerase having the amino acid sequence of SEQ ID NO: 1.

The present invention further relates to a process for producing UDP-GalNAc by acting an epimerase to UDP-GlcNAc, said epimerase being one having an amino acid sequence indicated by SEQ ID NO: 1 in the Sequence Listing or one having an amino acid sequence of SEQ ID NO: 1 which has undergone deletion, substitution and/or addition of one to several amino acid residues, and also having the same enzyme activity as the epimerase having the amino acid sequence of SEQ ID NO: 1.

BEST MODE FOR CARRYING OUT THE INVENTION

The UDP-glucose 4-epimerase used in the present invention is not subject to any specific restrictions as far as it is an enzyme derived from spore-forming bacteria and capable of catalyzing the following interconversion reactions (1) and (2):

(1) UDP-glucose ↔ UDP-galactose
(2) UDP-GlcNAc ↔ UDP-GalNAc

Such an UDP-glucose 4-epimerase can be prepared from spore-forming bacteria such as those belonging to the genus *Bacillus*.

Typical examples of the bacteria belonging to the genus *Bacillus* usable in the present invention are *B. subtilis, B. halodurans, B. megaterium, B. cereus*, and *B. stearothermophilus*. It is particularly notable that the UDP-glucose 4-epimerase gene (galE) derived from *B. subtilis* has already been cloned, and its DNA sequence has been reported (Gene Bank, Accession No. X99339). A *B. subtilis-derived* UDP-glucose 4-epimerase prepared by the usual recombinant DNA technology based on the disclosed DNA sequence of said cloned gene is preferably used in the present invention. This enzyme, as noted from the DNA sequence of its cloned gene, has an amino acid sequence shown as SEQ ID NO: 1 in the Sequence Listing. This enzyme is not the only enzyme usable in the present invention; it is also possible to use the enzymes having an amino acid sequence of SEQ ID NO: 1 which have undergone deletion, substitution and/or addition of one to several amino acid residues, and also having the same enzyme activity as the enzyme having the amino acid sequence of SEQ ID NO: 1.

A *B. subtilis-*derived UDP-glucose 4-epimerase gene can be obtained, for example, by synthesizing a probe based on the reported DNA sequence, and cloning a DNA fragment containing a gene encoding UDP-glucose 4-epimerase from chromosomal DNA of *B. subtilis*. The host used for cloning is not specified, but it is expedient to use *E. coli* as the host in view of handling advantage and easy availability. A gene of an enzyme having an amino acid sequence of SEQ ID NO: 1 which has undergone deletion, substitution and/or addition of one to several amino acid residues, and also having the same enzyme activity as the enzyme having the amino acid sequence of SEQ ID NO: 1 can be easily obtained by a pertinent method such as site-specific mutagenesis method, PCR method or ordinary hybridization method, based on the gene galE used.

For establishing a high expression system of the cloned gene, the DNA sequence of the DNA fragment cloned by applying Maxam-Gilbert method (Methods in Enzymology, 65, 499 (1983)), dideoxy chain termination method (Methods in Enzymology, 101, 20 (1983)) or other suitable method to specify the coding region of said gene, and an expression control signal (initiation signals of transcription and translation) is connected upstream of said region to make said gene capable of making expression in the microbial cells according to the host microorganism, thereby constituting a recombinant expression vector.

As the expression control signal used for bulk production of UDP-glucose 4-epimerase in *E. coli*, it is preferable to use a powerful initiation signals of transcription and translation which is capable of control intentionally and can drastically raise the yield of production of UDP-glucose 4-epimerase. Such powerful initiation signal of transcription is exemplified by lac promoter, trp promoter, tac promoter (Proc. Natl. Acad. Sci. USA., 80, 21 (1983); Gene, 20, 231 (1982)), and trc promoter (J. Biol. Chem., 260, 3539 (1985)).

As the vector, various types of plasmid vector, phage vactor, etc., can be used, but it is preferable to use a plasmid vector with a high copy number in the bacterial cells, which can be copied in the *E. coli* cells and has an appropriate drug resistance marker and a specific restriction enzyme cleavage site. Typical examples of such plasmid vector are pBR322 (Gene, 2, 95 (1975)), pUC18 and pUC19 (Gene, 33, 103 (1985)).

*E. coli* is transformed by using the prepared recombinant vector. As *E. coli* as the host cells, there can be used K12 strain, C600 strain, JM105 strain, or JM109 strain which is used for recombinant DNA experiments (Gene, 33, 103–119 (1985)).

Many methods have been reported for the transformation of *E. coli*, for example a method in which plasmid is introduced into the bacterial cells after treatment with calcium chloride at a low temperature (J. Mol. Biol., 53, 159 (1970)).

The obtained transformant is cultivated in a medium where this microorganism can grow, and is cultivated until the UDP-glucose 4-epimerase is accumulated in bulk in the bacterial cells by inducing expression of its genes. Cultivation of the transformant can be performed according to a conventional method using a medium containing nutrients necessary for the growth of said microorganism, such as carbon and nitrogen sources. For instance, cultivation may be carried out at 20 to 50° C. for about 10 to 50 hours, if necessary under aeration and stirring, using a medium commonly employed for the cultivation of *E. coli*, such as bouillon medium, LB medium (1% tryptone, 0.5% yeast extract and 1% common salt), or 2×YT medium (1.6% tryptone, 1% yeast extract and 0.5% common salt). In case plasmid is used as vector, a proper amount of a pertinent antibiotic (ampicillin, kanamycin, etc., depending on the drug resistance marker of plasmid) is added to the culture to prevent the dropout of plasmid during cultivation.

When the expression of the UDP-glucose 4-epimerase gene is required to be induced, the expression may be induced according to ordinary methods conventionally used for the promoter which is used as the expression control signal. For instance, when lac promoter, tac promoter and the like are used, isopropyl-β-D-thiogalactopyranoside (IPTG) as an expression inducing agent may be added at an appropriate amount to the culture at the middle stage. When the promoter used has constitutionally a transcriptional activity, the addition of such an agent may not be required.

The UDP-glucose 4-epimerase gene derived from the spore-forming bacteria other than *Bacillus subtilis* can be obtained by synthesizing a primer with reference to the DNA sequence of said *B. subtilis*-derived UDP-glucose 4-epimerase gene galE, searching for a DNA fragment with high homology with galE in chromosomal DNA of the spore-forming bacteria other than *B. subtilis*, with the synthesized primer serving as probe, and cloning this DNA fragment. As for *B. halodurans* which is also a bacterium belonging to the genus *Bacillus*, its whole genomic sequence has already been clarified (Extremophiles, 3(1), 21–28 (1999)), hence cloning thereof can be accomplished relatively easily with reference to said and other information. For preparing UDP-glucose 4-epimerase derived from a spore-forming bacterium other than *B. subtilis* by recombinant DNA technology using a cloned DNA fragment, it is possible to follow the same procedure as used for the preparation of the *B. subtilis-derived* UDP-glucose 4-epimerase gene galE described above.

Alternatively, UDP-glucose 4-epimerase derived from a spore-forming bacterium other than *B. subtilis* may be prepared by cultivating the bacterium in the ordinary way and purifying the cultures. More specifically, the bacterium is cultivated in an SCD, standard agar or nutrient agar medium. Cultivation may be carried out according to a conventional liquid cultivation method at a temperature suited for the growth of the bacterium to be cultivated, such as 25 to 65° C., if necessary under aeration and stirring. From the thus obtained cultures, the bacterial cells are recovered by suitable means such as membrane separation or centrifugation, and the collected bacterial cells are destroyed by ultrasonication or other suitable means, and then subjected to one or a combination of various treatments such as heat treatment, ammonium sulfate fractionation, dialysis, chromatographies (ion exchange, gel filtration, etc.), to obtain the objective UDP-glucose 4-epimerase. Trace and confirmation of UDP-glucose 4-epimerase in the purification step can be conducted, for example, according to the UDP-glucose 4-epimerase activity measuring method described in the Examples of the present specification.

Regarding the mode of use in application of the thus obtained UDP-glucose 4-epimerase to the method of the present invention, in the case of UDP-glucose 4-epimerase obtained by recombinant DNA technology, it is possible to put the said transformant directly to use, or the transformant may be used in the form of a treated product thereof or enzyme obtained by purifying the treated product. In case UDP-glucose 4-epimerase was prepared according to a conventional purification method without using recombinant DNA technology, it may be applied to use in the form as it is.

In case of utilizing a transformant as UDP-glucose 4-epimerase, it is possible to use, for instance, the microbial cells recovered from the cultures of the transformant by solid/liquid separating means such as centrifugation or membrane separation. Example of treated cell products of the transformant include destructed cell products as well as modified products of cell wall or plasma membranes of the cell obtained from said recovered microbial cells through the ordinary treatments such as mechanical destruction (destroyed by Waring blender, French press, homogenizer, mortar, etc.), freezing-thawing, autolysis, drying (lyophilization, air drying, etc.), enzymatic treatments (treatments with lysozyme, etc.), ultrasonication, and chemical treatments (treatments with an acid, an alkali, etc.). Among the enzymes obtained by purifying said treated products are crude or purified enzymes obtained from said microbial cell treated products by subjecting the fractions having the enzyme activities to an ordinary enzyme purifying treatment (salting out, isoelectric precipitation, organic solvent precipitation, dialysis, chromatography, etc.)

The conversion reaction of from UDP-GlcNAc to UDP-GalNAc using such UDP-glucose 4-epimerase, or epimerization from UDP-GlcNAc to UDP-GalNAc can be accomplished, for example, under the following conditions.

The UDP-GlcNAc used for the reaction is already commercially available, and the commercial product can be used in the present invention. The concentration of UDP-GlcNAc can be properly set, for example, in the range of 1 to 5,000 mM, preferably 10 to 1,000 mM. The concentration of UDP-glucose 4-epimerase added to the reaction solution can also be properly set, for example, in the range of 0.001 to 100 units/ml.

The above reaction can be carried out in a suitable buffer such as Tris-hydrochloric acid or potassium phosphate (pH 7–9, preferably 7.5–8.5) at 60° C. or below, preferably 15 to 50° C., for about 1 to 50 hours, if necessary with stirring.

Preferably, magnesium is added as desired to the above reaction solution. As magnesium, there can be used magnesium salts of inorganic acids such as magnesium sulfate, magnesium nitrate and magnesium chloride, and magnesium salts of organic acids such as magnesium citrate. The concentration of magnesium can be properly set in the range of 5 to 50 mM.

In case the produced UDP-GalNAc needs to be isolated from the mixture with UDP-GlcNAc, the ordinarily used sugar nucleotide purification methods (e.g., various chromatographies such as ion exchange chromatography, adsorption chromatography, affinity chromatography and gel filtration, methods utilizing distribution between two liquid phases such as countercurrent distribution and countercurrent extraction, methods utilizing the difference in solubility such as concentration, cooling and addition of an organic solvent, and salting out) can be used independently or in a suitable combination.

The UDP-GalNAc supply system in the present invention is comprised of UDP-GlcNAc and UDP-glucose 4-epimerase derived from a spore-forming bacterium. This supply system, when linked, for instance, to a glycosyl transferase (GalNAc transferase) alone or to a combination thereof with an UDP-GlcNAc regeneration system, can be utilized for the synthesis of oligosaccharides containing N-acetylgalactosamine (JP-A-7-79792).

EXAMPLES

The present invention will be explained in more detail with reference to an example thereof, but it will be obvious that the present invention is not limited to this example. In the Example which follows, determination of UDP-GalNAc in the reaction solution was made by HPLC using YMC Corp.'s ODS-AQ312 columns for separation, and a 1 mM tetrabutylammonium and 50 mM magnesium acetate solution as eluent. Preparation of DNA, cleavage by a restriction enzyme, DNA ligation by T4DNA ligase, and transformation of E. coli were all conducted according to the methods described in Sambrook et al: Molecular Cloning, A Laboratory Manual, Second Ed. Cold Spring Harbor Laboratory, Cold Spring Harbor, N.Y. (1989). The restriction enzyme, AmpliTaqDNA polymerase and T4DNA ligase were obtained from Takara Co., Ltd.

Example 1

(1) Cloning of UDP-Glucose 4-Epimerase Gene

Chromosomal DNA of B. subtilis 168M (ATCC 27370) was prepared by Saito-Miura method (Biochim. Biophys. Acta., 72, 619 (1963)). Rendering this DNA temperate and using the following two types of primer DNA (SEQ ID NOs: 2 and 3 in the Sequence Listing), the B. subtilis UDP-glucose 4-epimerase (galE) gene was amplified by PCR.

Primer (A):
5'-GATCTAGAAACCTCTATCGAATTGCTGG-3'

Primer (B):
5'-AACTGCAGGCCTCCATTCTTATTCCGCACT-3'

Amplification of the galE gene by PCR was performed by repeating 25 times the steps of thermal denaturation (94° C., 1 min), annealing (57° C., 15 min) and polymerisation (72° C., 3 min) of the reaction solution [containing in 100 µl thereof 50 mM potassium chloride, 10 mM Tris-hydrochloric acid (pH 8.3), 1.5 mM magnesium chloride, 0.001% gelatin, 0.2 mM DNTP, 0.1 µg temperate DNA, Primer DNAs (A) and (B) (0.2 µM respectively) and 2.5 units of AmpliTaq DNA polymerase] by using DNA Thermal Cycler of Perkin-Elmer Cetus Instrument Co., Ltd.

After gene amplification, the reaction solution was treated with a phenol/chloroform (1:1) mixed solution, and to the water-soluble fraction was added ethanol in an amount twice to thereby precipitate DNA. The precipitated and recovered DNA was separated by agarose gel electrophoresis according to the method in the literature (Molecular Cloning, mentioned above) to purify the DNA fragments of 1.2 kb. This DNA was cleaved with restriction enzymes XbaI and PstI, and then ligated with plasmid pTrc99A (obtained from Pharmacia Biotech) by using T4DNA ligase which plasmid had been digested with said restriction enzymes XbaI and PstI. E. coli JM109 strain (obtained from Takara Co. Ltd.) was transformed by using the ligation reaction solution, and plasmid pTrc-galE-1 was isolated from the obtained ampicillin resistant transformant. This plasmid pTrc-galE-1 is a product obtained by inserting into pTrc99A, at the XbaI-PstI cleavage sites downstream of the trc promoter, an XbaI-PstI DNA fragment containing the promoter and structural gene of B. subtilis galE gene.

(2) Preparation of UDP-Glucose 4-Epimerase

E. coli JM109 strain harboring plasmid pTrc-galE-1 was inoculated to 500 ml of 2×YT medium containing 100 µg/ml of ampicillin and subjected to shaking culture at 37° C. When the bacterial cell culture reached 4×10$^8$ cells/ml, IPTG was added to the culture solution so that it would have a final concentration of 1 mM, and shaking culture was further continued at 37° C. for 5 hours. After cultivation, the bacterial cells were collected by centrifugation (9.000×g, 10 min) and suspended in 50 ml of a buffer solution (20 mM Tris-hydrochloric acid (pH 8.0) and 2 mM EDTA). The bacterial cells were destroyed by ultrasonication and further centrifuged (20,000×g, 10 min) to remove the cellular residue.

The thus obtained supernatant fraction was provided as the enzyme preparation, and UDP-glucose 4-epimerase activity and UDP-GlcNAc 4-epimerase activity in this enzyme preparation were determined. The results are shown in Table 1 along with the results of the control bacterium (E. coli MJM109 strain harboring pTrc99A). The unit of epimerase activity in the present invention was calculated as follows.

i) Determination of UDP-Glucose 4-Epimerase Activity and Method of Calculating the Unit of Activity The enzyme preparation was added to a 50 mM Tris-hydrochloric acid buffer (pH 8.0) containing 2.5 mM magnesium chloride and 10 mM UDP-glucose and incubated at 37° C. to perform the reaction, followed by 5-minute boiling to inactivate the enzyme. UDP-galactose in the reaction solution was determined by HPLC. The activity that forms 1 µmol of UDP-galactose at 37° C. in one minute is defined as one unit.

ii) Determination of UDP-GlcNAc 4-Epimerase Activity and Method of Calculating the Unit of Activity The enzyme preparation was added to a 50 mM Tris-hydrochloric acid buffer (pH 8.0) containing 2.5 mM magnesium chloride and 10 mM UDP-GlcNAc and incubated at 37° C. to conduct the reaction, followed by 5-minute boiling to inactivate the enzyme. UDP-GalNAc in the reaction solution was determined by HPLC. The activity that forms 1 µmol of UDP-GalNAc at 37° C. in one minute is defined as one unit.

TABLE 1

| Plasmid | Epimerase activity (units/mg protein) | |
|---|---|---|
| | UDP-glucose 4-epimerase | UDP-GlcNAc 4-epimerase |
| pTrc99A | 0.011 | <0.001 |
| pTrc-galE-1 | 2.06 | 1.09 |

(3) Preparation of Partially Purified Product of UDP-Glucose 4-Epimerase

To the enzyme preparation obtained in (2) above, ammonium sulfate was added in such an amount as to provide 40% saturation, and the mixture was stirred overnight at 4° C. and then centrifuged (20,000×g, 10 min) to remove the precipitate. To the obtained supernatant fraction, ammonium sulfate was again added to provide 80% saturation, and the mixture was stirred overnight at 4° C. and then centrifuged (20,000× g, 10 min). The precipitated fraction was dissolved in 5 ml of 20 mM Tris-hydrochloric acid (pH 8.0) and dialyzed twice in 1 liter of said buffer solution. The thus obtained sample was used as the enzyme solution and subjected to the synthesis reaction described in (4) below. The UDP-GlcNAc 4-epimerase activity in this enzyme solution was 4.38 units/mg protein.

(4) Synthesis of UDP-GalNAc 0.212 unit of the enzyme solution obtained in (3) above was added to 500 µl of 100 mM Tris-hydrochloric acid buffer (pH 8.0) containing 180 mM UDP-GlcNAc and 10 mM magnesium chloride and reacted at 37° C. for 21 hours. HPLC analysis of the reaction solution indicated the formation of 50.38 mM UDP-GalNAc.

INDUSTRIAL APPLICABILITY

Any of the hitherto reported UDP-GalNAc preparation methods using UDP-GlcNAc 4-epimerase was far from being practical for the reasons such as scanty production of the enzyme in the animal tissues and bacterial cells.

The present inventors found that UDP-glucose 4-epimerase derived from the bacteria having a spore forming faculty is not only capable of inducing a reaction of converting UDP-glucose to UDP-galactose but also has an activity to catalyze the conversion reaction from UDP-GlcNAc to UDP-GalNAc. This disclosure has made it possible for the first time to utilize the conversion reaction of from UDP-GlcNAc to UDP-GalNAc for practical applications.

What is claimed is:

1. A method of converting uridine diphosphate N-acetylglucosamine to uridine diphosphate N-acetylgalactosamine by using an epimerase, said epimerase being uridine diphosphate glucose 4-epimerase derived from a spore-forming bacterium.

2. The method according to claim 1, wherein the spore-forming bacterium is a bacterium belonging to the genus *Bacillus*.

3. The method according to claim 1, wherein the spore-forming bacterium is *Bacillus subtilis*.

4. The method according to claim 1, wherein the uridine diphosphate glucose 4-epimerase is recombinantly produced using an uridine diphosphate glucose 4-epimerase gene derived from *Bacillus subtilis*.

5. An uridine diphosphate N-acetylgalactosamine supply system comprising uridine diphosphate N-acetylglucosamine and an uridine diphosphate glucose 4-epimerase derived from a spore-forming bacterium.

6. The supply system according to claim 5, wherein the spore-forming bacterium is a bacterium belonging to the genus *Bacillus*.

7. The supply system according to claim 5, wherein the spore-forming bacterium is *Bacillus subtilis*.

8. The supply system according to claim 5, wherein the uridine diphosphate glucose 4-epimerase is recombinantly produced using an uridine diphosphate glucose 4-epimerase gene derived from *Bacillus subtilis*.

9. A process for producing uridine diphosphate N-acetylgalactosamine by reacting an epimerase with uridine diphosphate N-acetylglucosamine, said epimerase being uridine diphosphate glucose 4-epimerase derived from a spore-forming bacterium.

10. The process according to claim 9, wherein the spore-forming bacterium is a bacterium belonging to the genus *Bacillus*.

11. The process according to claim 9, wherein the spore-forming bacterium is *Bacillus subtilis*.

12. The process according to claim 9, wherein the uridine diphosphate glucose 4-epimerase is recombinantly produced using an uridine diphosphate glucose 4-epimerase gene derived from *Bacillus subtilis*.

13. A method of converting uridine diphosphate N-acetylglucosamine to uridine diphosphate N-acetylgalactosamine by using an epimerase, said epimerase having an amino acid sequence of SEQ ID NO: 1, or an amino acid sequence of SEQ ID NO: 1 which has undergone deletion, substitution and/or addition of one to several amino acid residues, and also having the same enzyme activity as the epimerase having the amino acid sequence of SEQ ID NO: 1.

14. The method according to claim 13, wherein the epimerase is recombinantly produced.

15. An uridine diphosphate N-acetylgalactosamine supply system comprising uridine diphosphate N-acetylglucosamine and an epimerase having an amino acid sequence of SEQ ID NO: 1, or an epimerase having an amino acid sequence of SEQ ID NO: 1 which has undergone deletion, substitution and/or addition of one to several amino acid residues, and also having the same enzyme activity as the epimerase having the amino acid sequence of SEQ ID NO: 1.

16. The supply system according to claim 15, wherein the epimerase is recombinantly produced.

17. A process for producing uridine diphosphate N-acetylgalactosamine by reacting an epimerase with uridine diphosphate N-acetylglucosamine, said epimerase having an amino acid sequence of SEQ ID NO: 1 or an amino acid sequence of SEQ ID NO: 1 which has undergone deletion, substitution and/or addition of one to several amino acid residues, and also having the same enzyme activity as the epimerase having the amino acid sequence of SEQ ID NO: 1.

18. The process according to claim 17, wherein the epimerase is recombinantly produced.

* * * * *